United States Patent [19]

Harper et al.

[11] Patent Number: 4,619,409

[45] Date of Patent: Oct. 28, 1986

[54] HOSPITAL WASTE DISPOSAL SYSTEM

[75] Inventors: Allan C. Harper; Joseph H. Wilson, both of Indianapolis; Randall G. McKee, Yorktown; David N. Lasiter, Indianapolis, all of Ind.

[73] Assignee: Medical Safetec, Inc., Indianapolis, Ind.

[21] Appl. No.: 658,701

[22] Filed: Oct. 9, 1984

[51] Int. Cl.[4] .................... B02C 9/04; B02C 19/12
[52] U.S. Cl. .......................................... 241/38; 241/34; 241/99; 241/186.2; 241/188 R; 241/285 R; 241/285 A; 241/285 B; 384/135
[58] Field of Search ............... 198/592, 628, 950; 241/34, 36, 38, 41, 99, 186 R, 186.2, 187, 186.3, 188 R, 189, 190, 235, 285 R, 285 A, 285 B, DIG. 14; 414/222, 225

[56]  References Cited

U.S. PATENT DOCUMENTS

| | | | |
|---|---|---|---|
| 2,540,021 | 1/1951 | Wright | 241/187 |
| 2,823,868 | 2/1958 | Scherer | 241/DIG. 14 |
| 3,071,296 | 1/1963 | Frey et al. | 384/135 X |
| 3,825,192 | 7/1974 | Knight | 241/186 R |
| 4,188,861 | 2/1980 | Kroeze et al. | 198/592 X |
| 4,346,850 | 8/1982 | Westergaard | 241/36 |
| 4,401,205 | 8/1983 | Komossa et al. | 241/34 X |

Primary Examiner—Howard N. Goldberg
Assistant Examiner—Timothy V. Eley
Attorney, Agent, or Firm—Dick and Harris

[57]  ABSTRACT

A system for disposing of large amounts of infectious hospital waste includes a generally sealed enclosure containing an apparatus for delivery, disintegration, and decontamination of waste materials. A dual conveyor arrangement provides a positive delivery of large waste containers to be disposed to a disintegrator while preventing material from being thrown from the disintegrator. The disintegrator comprises two, large, counter-rotating hammermills capable of effectively disintegrating articles of substantial size. The system enclosure is maintained at a negative pressure and adapted to prevent escape of airborne contamination from the system. A variety of protective features is also incorporated into the system to clear the disintegrator in cases of overload, to avoid power surges upon system start-up, and to effect an orderly shutdown of the system.

22 Claims, 9 Drawing Figures

HOSPITAL WASTE DISPOSAL SYSTEM

BACKGROUND OF THE INVENTION

This invention relates to a system for disposing of infectious hospital waste such as hypodermic syringes, bottles, cans, containers, and other potentially hazardous materials and, more particularly, to a system for disintegrating and disinfecting large containers of such solid hospital waste.

Hazardous waste disposal is a very serious problem that has received substantial media attention in recent years. Many governmental jurisdictions have already enacted very strict hazardous waste disposal laws and further legislation in this area is anticipated. Hospitals and other health care facilities generate substantial amounts of potentially hazardous contaminated materials and are acutely aware of the need to process and dispose of these materials in the proper manner.

Conventional disposal procedures, however, have not proven to be fully satisfactory. For example, procedures which simply reduce the size of the contaminated materials such as cutting or compaction are inadequate because the materials remain contaminated unless they are subjected to a relatively expensive autoclaving process prior to the size reduction. Procedures resulting in incineration of the waste materials, although effective in both reducing the size of and decontaminating the materials, are not fully satisfactory because they require regular servicing and cleaning and provide some danger of toxic gas emission.

U.S. Pat. No. 3,926,379 discloses a syringe disintegrator in which syringes are both pulverized and disinfected. Such a system, however, has been shown to be noisy, unreliable, and unsuitable for use in the hospital areas where it was needed. Operation of the system also resulted in a potentially bacteria-laden exhaust from the apparatus, and the apparatus was generally incapable of accepting contaminated articles of relatively large size such as are commonly generated in a hospital environment and require effective disposal.

SUMMARY OF THE INVENTION

The present invention relates to a waste disposal system that is capable of processing essentially all infectious waste materials that are likely to be generated by a hospital or other health care facility. The overall system includes a generally sealed cabinet which contains structure for disintegrating and decontaminating waste materials fed into the cabinet, a feeding means for feeding contaminated waste materials into the cabinet in a safe, efficient manner for processing, a separator for separating the disintegrated solid waste materials from the decontaminating fluid, and a system control for controlling and monitoring the operation of the overall system.

In accordance with one aspect of the invention, the feeding means is operated by the system control and includes a first conveyor portion which comprises a continuous conveyor belt upon which the contaminated materials to be disposed of may be placed and a second conveyor portion for receiving the materials from the first conveyor portion and for directing them into the cabinet and disintegrating means. The first conveyor portion makes it possible for a person who wishes to dispose of a contaminated article to simply place the contaminated article on its conveyor belt and leave. It is not necessary for the person to wait until a previous article has been processed in the cabinet or for the person to know how to operate this system. The system control insures that the waste will be fed into the cabinet at a high, effective rate based on the type of materials being destroyed to reduce the danger of overfeeding that was present in prior systems.

The system also includes means for maintaining a negative pressure both within the cabinet and within the feeding means to help prevent contaminated air from escaping from within the system into the surrounding atmosphere.

The system further includes a novel disintegration system comprising two high-speed, heavy-duty, counter-rotating hammermills which operate as a unit to permit rapid and reliable disintegration of large-sized articles; for example, sizes up to 16 inches square (or diameter) by 48 inches in length.

The system additionally incorporates a variety of features to insure safe, reliable operation of the system. For example, the system is provided with a "softened" starting system to eliminate line power surges which can affect the operation of critically important electrical equipment within the hospital. Means are also provided to monitor the disintegration unit and to take quick action to clear an overload condition therein or, if necessary, to shut down the system before serious damage can result. Furthermore, means are provided to shut down the system in an orderly manner to insure that all contaminated materials are properly processed and to avoid leakage of contaminant from the system.

Further features and advantages of the invention will become apparent hereinafter in connection with the detailed description of the presently preferred embodiment taken together with the following drawings.

DETAILED DESCRIPTION OF THE PREFERRED EMBODIMENT

Figure 1:
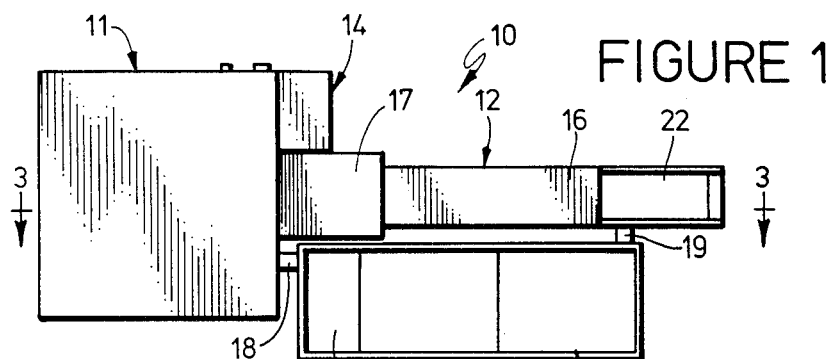
FIG. 1 is a top view of the waste disposal system according to a presently preferred embodiment of the invention.
Figure 2:
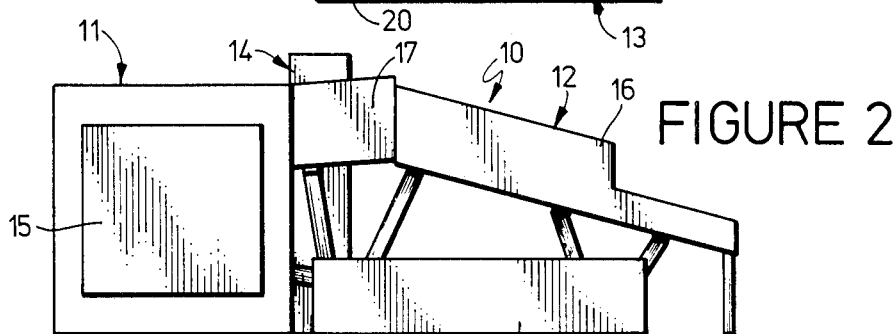
FIG. 2 is a plan view of the system of FIG. 1.

FIGS. 1 and 2 illustrate the overall waste disposal system according to a preferred embodiment of the present invention. The system is generally designated by reference numeral 10 and includes a generally sealed cabinet 11 within which the waste materials are disintegrated and decontaminated, a feeding means 12 for automatically feeding contaminated waste materials into the cabinet to be processed, a generally closed separator 13 for separating the processed waste materials from the decontaminating fluid, and a system control means 14 for monitoring and controlling the overall operation of the system.

The feeding means 12 generally comprises a first conveyor portion 16 for receiving contaminated articles to be disposed of and a second conveyor portion 17 for transferring the articles from the first conveyor portion into the cabinet 11 for disintegration.

The cabinet 11 generally includes a disintegrator for disintegrating and decontaminating solid waste; means for maintaining a negative pressure both within the cabinet and the feeding means; and various electrical and pneumatic components to operate the disintegrator and the blower. The cabinet is preferably provided with panels, e.g., panel 15, which are easily removable for servicing purposes.

The separator 13 is connected to the cabinet 11 and communicates with the disintegrator therein through conduit 18. The separator is designed to separate the disintegrated, decontaminated waste from the disinfectant solution used to decontaminate the waste and to deliver the disinfectant solution to a public sewer via a conduit 19. The separator 13 also includes a hinged top 20 to permit the disinfected solid waste to be periodically removed from the separator and placed in sealed containers for disposal.

The system control means 14 provides an electrical control circuit including a plurality of solidstate circuits and relays which permit the system to be operated by hospital personnel by means of a simple push-button control system. The controls include microcomputer programmable controller means and associated circuitry to monitor and control the overall system to provide safe, efficient, reliable operation at all times.

Figure 3:
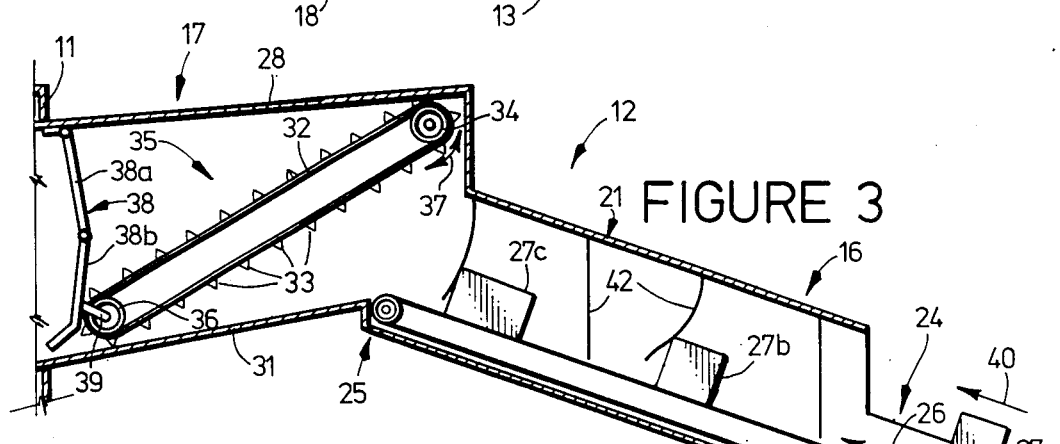
FIG. 3 is a cross-sectional view of the feeding means of FIGS. 1 and 2.

FIG. 3 is a cross-sectional view of the feeding means 12 for receiving contaminated waste products and for automatically feeding such products into the cabinet 11 to be processed. As indicated previously, the feeding means is comprised of two portions: a first conveyor portion 16 to receive the contaminated articles and a second conveyor portion 17 for transferring the articles from the first conveyor portion into the cabinet 11 and the disintegrator means.

First conveyor portion 16 comprises a first conveyor housing portion 21 within which is supported a continuous belt 22; for example, a fiber-reinforced polyurethane belt. First conveyor portion housing 21 comprises an elongated housing of generally rectangular cross section. A section of the housing, however, is not enclosed to define an input portion 24, providing access to the conveyor belt 22 so that contaminated articles may be easily placed thereon. The housing 21 and the continuous belt 22 supported therein are inclined at an upwardly extending angle such that articles to be processed will be carried upwardly along the length of the belt in the direction indicated by arrow 26 from the input end 24 to the output end 25 thereof.

As shown in FIG. 3, continuous belt 22 is capable of supporting a plurality of articles at one time (three articles 27a, 27b, and 27c are shown, for example, in FIG. 3). Accordingly, when a person wishes to dispose of a contaminated article, he can simply place it on the conveyor 22 and leave. It is not necessary for him to wait until a previous article has been processed in the cabinet.

Figure 4:
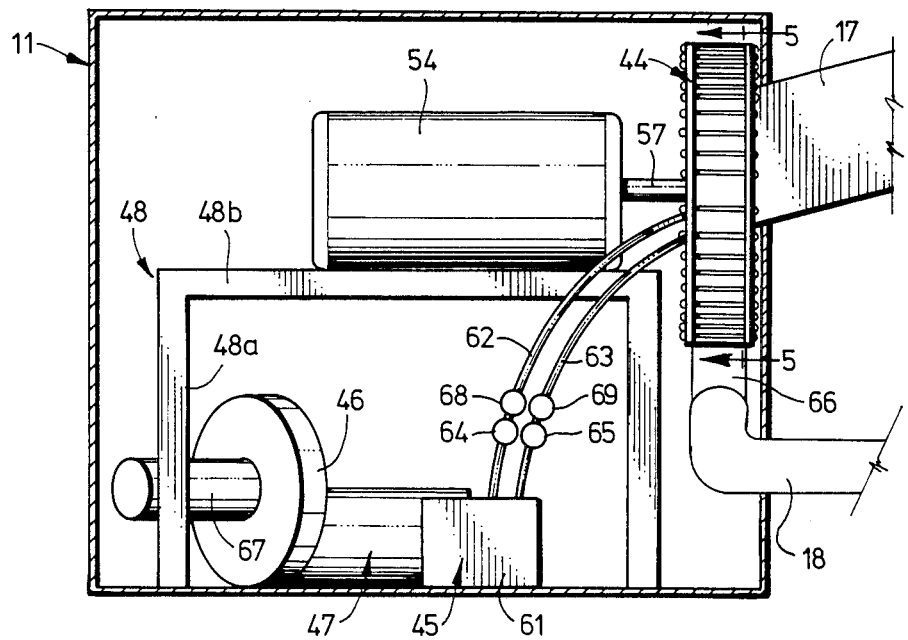
FIG. 4 is a schematic view of the interior of the cabinet of the system of FIGS. 1 and 2 illustrating the arrangement of the major components therein.

When a contaminated article has been transported to the output end 25 of the first conveyor portion 16 by the belt 22, the article is transferred onto a slide surface 31 supported within the second conveyor portion 17. The second conveyor portion 17 comprises a second conveyor portion housing 28, also of generally rectangular cross section, which is attached to both the first conveyor portion housing 21 and to the cabinet 11. Housing 28 is inclined downwardly at a slight angle and is provided to transfer the articles from the first conveyor portion 16 into the cabinet 11 and into the disintegrator means 44 (FIG. 4). To deliver the contaminated articles to the disintegrator, a driven belt assembly 35 comprising an endless belt 32 is supported within second conveyor portion housing above the slide 31 with its upper end so located that it can engage large waste containers, preferably while they are still in contact with the first conveyor belt 22. Belt 32 comprises an elastomeric belt having a plurality of teeth 33 provided thereon along the length of the belt, and its function is to engage the articles and move or pull them, one at a time, from the belt 22 into the cabinet 11. Belt assembly 35 is preferably driven by a suitable electric motor (not shown). As illustrated in FIG. 3, belt assembly 35 is positioned such that a portion thereof extends over belt 22 in first conveyor portion 16. Accordingly, when an article approaches the output end 25 of first conveyor portion 16, it will be engaged by the belt 32 of belt assembly 35 and pulled onto slide 31 of the second conveyor portion 17.

Figure 3A:
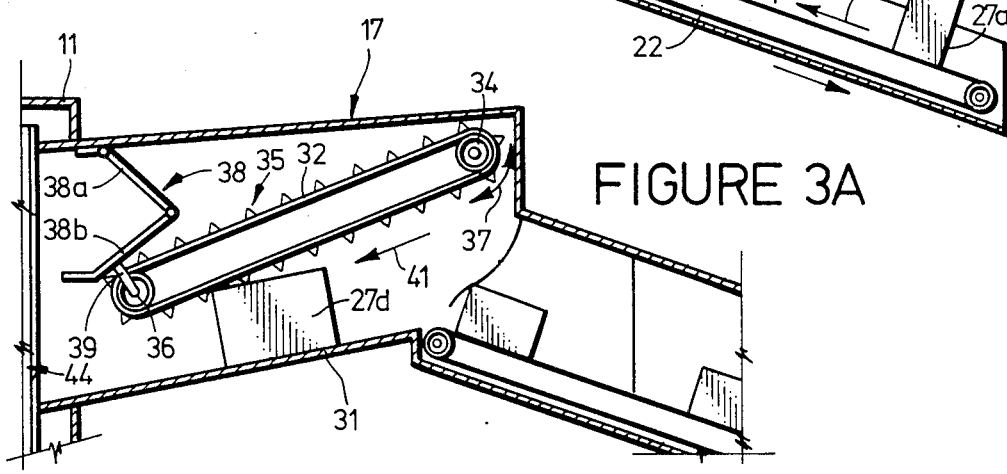
FIG. 3A illustrates an alternative position of the second conveyor portion of the feeding means of FIG. 3.

Belt 32 is supported around a pair of rollers 34 and 36, and the entire belt assembly 35 is mounted for pivotal movement around the axis of roller 34 as indicated by arrow 37. Belt assembly 35 is positioned relative to continuous belt 22 to insure that all contaminated articles regardless of size will be reliably engaged by belt 32. Gravity and the weight of the belt assembly maintain roller 36 pressed against slide 31 as shown in FIG. 3. An articulated door 38 comprising door portions 38a and 38b is coupled to roller 36 by a pivotable coupling 39. In the position shown in FIG. 3, when the belt assembly is in its down position, the door will fully close the entrance into cabinet 11. When, however, an article, such as article 27d in FIG. 3A, is encountered by the belt assembly 35 and is pulled toward the door 38 by the movement of toothed belt 32, as indicated by arrow 41, the belt assembly will be pushed up by the article against gravity, pivoting about the axis of roller 34, as indicated by arrow 37. As the assembly 35 lifts up, coupling 39 will carry the articulated door 38 upwardly, opening it to allow the article 27d to pass through into the cabinet 11. When the article has passed into the cabinet, the belt assembly 35 will return to the FIG. 3 position, closing door 38 as it does so.

Thus, with the present invention, door 38, providing access to cabinet 11, will open only when an article is being fed into the cabinet and will remain closed at all other times. This will help prevent broken materials from escaping from within the cabinet into the feeding means. Also, the door 38 will only open to the extent necessary to allow a particular article to pass. Larger articles will force the belt assembly 35 and, hence, door 38 upwardly to a greater extent than smaller articles. In addition, the constant force applied by the weight of the belt assembly 35 will provide firm contact of the belt 32 against an article being fed to assure that the article will be reliably fed into the cabinet 11 without slippage.

Feeding means 12 is controlled by system control 14 which will automatically actuate the system to feed articles into the cabinet at the proper rate as a function of the size and type of articles being processed. This helps to reduce the risk of overloading the disintegrator within cabinet 11.

Feeding means 12 is adapted to be maintained at a negative pressure at all times during operation of the waste disposal system by a blower means provided within the cabinet 11. Thus, there will be a continuous inflow of air into the housing, as indicated by arrow 40, which air flow helps prevent bacteria or other airborne contamination from escaping into the atmosphere around the system. For further protection, a plurality of "spit back" curtains 42 are provided within first conveyor portion housing 21 as illustrated. As the articles 27 are carried up the conveyor 22, they will simply move the curtains aside as they pass; and upon their passing, the curtains will fall back into position to generally close the housing, reducing air entry and maintaining the negative air pressure of the system.

FIG. 4 schematically illustrates the interior of the cabinet 11 to show the arrangement of the major components therein. Such components include a disintegrator 44, a disinfectant source 45, a source of negative pressure 46, and a pneumatic power source 47. As shown in FIG. 4, the contaminated waste products enter into the cabinet 11 and fall directly into the disintegrator 44 through an input opening 43 provided in the disintegration housing 73 (see FIG. 5). The disintegrator is illustrated in greater detail in FIGS. 5–7 and comprises a pair of counter-rotating hammermills driven by two large electric motors through appropriate couplings. One of the motors 54 and one of the couplings 57 are visible in FIG. 4. In the embodiment illustrated, each motor comprises a large, 100-horsepower, three-phase, 3,500 rpm motor of the type manufactured, for example, by Marathon or Baldor of Fort Smith, Ark., and is coupled to its associated hammermill with a torque-limiting coupling to prevent stalling in the event of a jammed hammermill. The hammermills and the motors are securely mounted to the rigid framework 48 as illustrated.

The source of disinfectant 45 includes a container 61 from which a pair of hoses 62 and 63 extends to carry disinfectant fluid, for example, sodium hypochlorite solution, from the container into the second conveyor portion 17 and the disintegrator 44 by means of electrically driven pumps 64 and 65, respectively. Means are also provided to introduce water into the second conveyor portion 17. This can be accomplished by introducing water from the hospital water system into lines 62 and 63 by appropriate valve means (not shown) operated by the system control 14 to provide a disinfectant-water solution to the second conveyor portion 17 and the disintegrator 44 during operation of the system.

Within the disintegrator 44, the waste is disintegrated into particulate form and decontaminated by the disinfectant solution. The particulate waste and disinfectant solution are then directed outwardly of the disintegrator through a transition chute 66 and to the separator 13 through conduit 18.

Also contained within the cabinet 11 is a blower 46 driven by a motor 67. The blower 46 is driven in such a direction that it exhausts the interior of the cabinet 11 as well as the housings 21 and 28 of the feeding means through inlet opening 43 to a hospital ventilator leading outside of the hospital. The interior of cabinet 11 and the interior of feeding means housing portions 21 and 28 are thus provided with a negative pressure which is greater than the positive pressure created by the rapidly rotating hammermills, preventing airborne contamination that may be created in the operation of the disintegrator from escaping from the cabinet or the feeding means. The cabinet 11 preferably includes a HEPA bacterial filter in the exhaust to prevent bacteria from being carried from the cabinet with the exhaust of blower 46. The HEPA filter comprises a "high efficiency particulate arrester" filter typically used to entrap bacterial particulate in, for example, clean room environments, with such filters often fabricated of microglass fibers and organic binders.

An electrically powered pneumatic pump or pressure source 47 is provided within cabinet 11 to actuate pneumatic components, such as pneumatic cylinders, and to operate movable components of the waste input 43 and disintegrator 44 through various pneumatic hoses which are not illustrated in FIG. 4 for purposes of clarity.

The structural framework 48 for the disintegrator 44 and its motors may be constructed by welding together I-shaped iron beams to provide four legs 48a and transverse beams 48b to position and support rigidly the disintegrator components within the cabinet 11. The legs 48a of the supporting structure 48 for the disintegrator 44 are preferably bolted directly to the hospital floor through suitable vibration-damping mountings.

Figure 5:
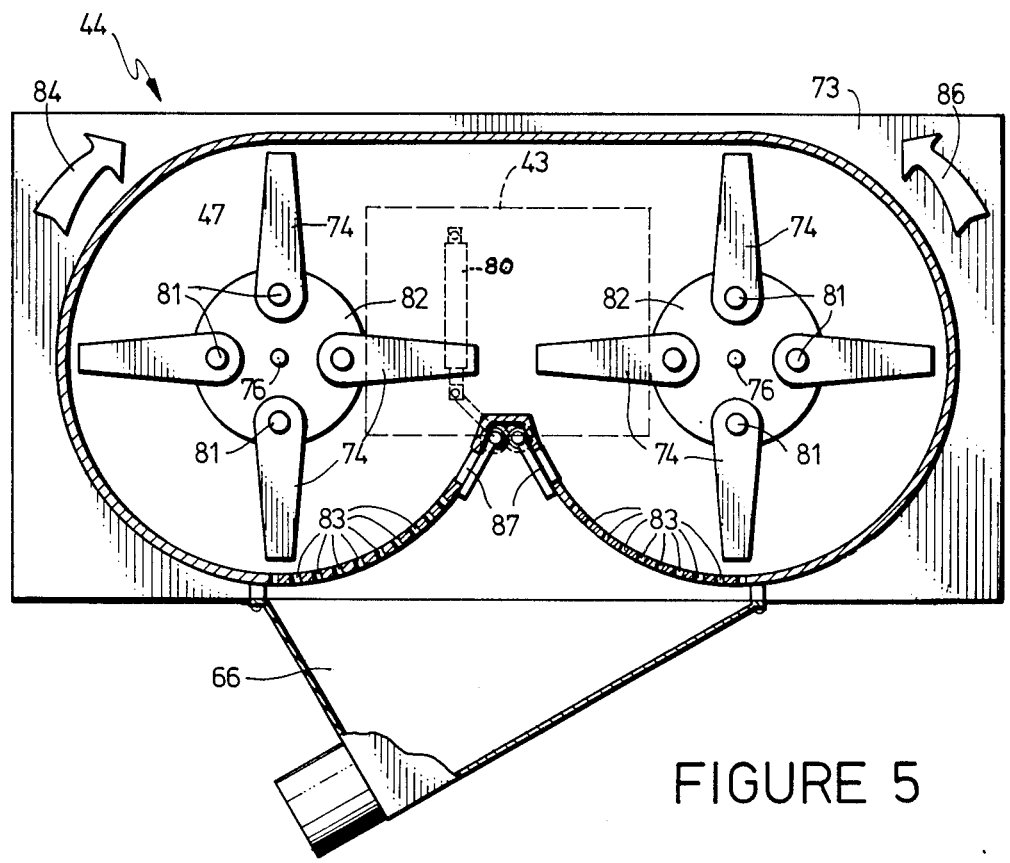
FIG. 5 schematically illustrates a cross-sectional view of the disintegrator means of the present invention looking in the direction of arrow 5—5 in FIG. 4.
Figure 6:
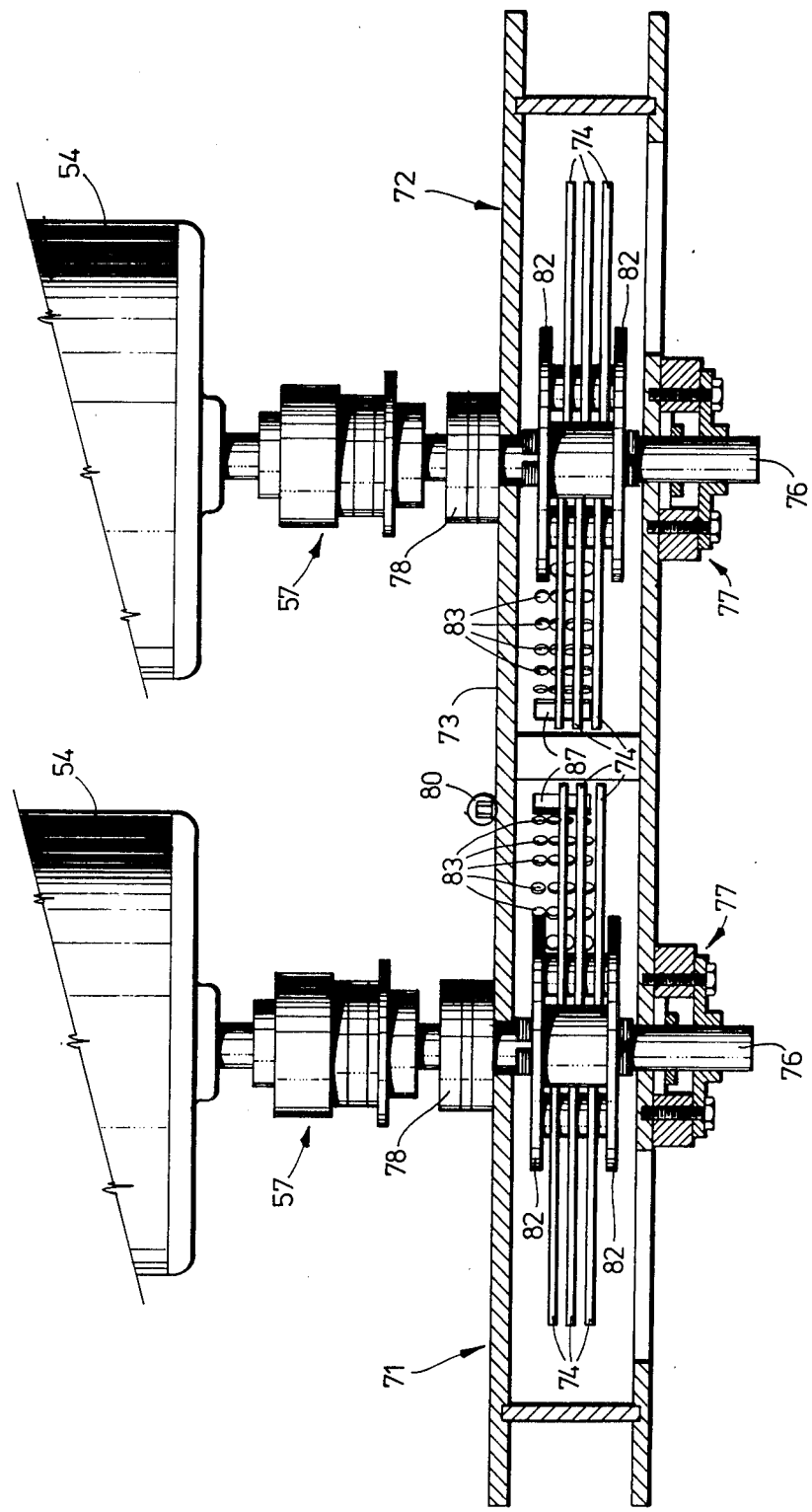
FIG. 6 is a partial cross-sectional top view of the disintegrator means of FIG. 5.
Figure 7:
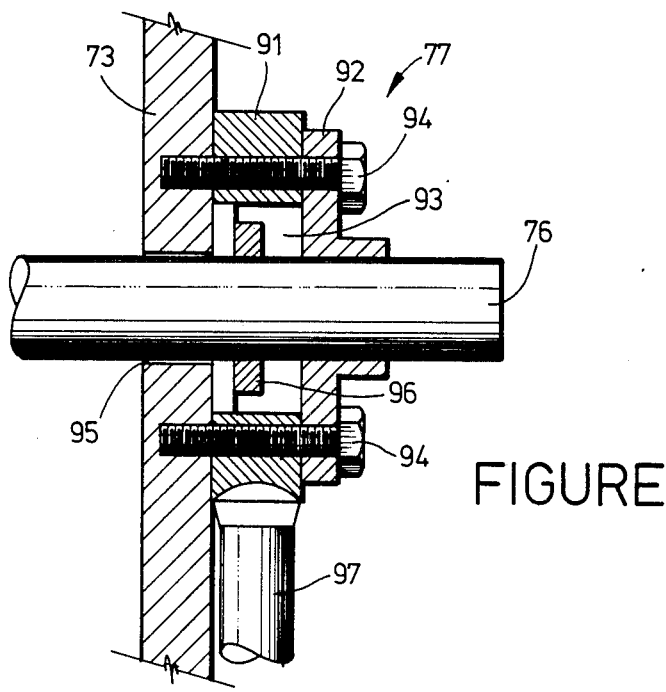
FIG. 7 is a cross-sectional view of the bearing means of FIG. 6.

The disintegrator 44 is shown in greater detail in FIGS. 5–7. The structure comprises a pair of counter-rotating hammermill assemblies 71 and 72 supported within a disintegrator housing 73. An opening 43 is provided in the wall of the disintegrator housing though which waste materials from feeding means 12 fall into the disintegrator 44.

The hammermills 71 and 72 are essentially identical, and each comprises a plurality of hammer components 74 hingedly carried about rotating shafts 76 coupled to the motor drive shafts 57. The leading edges of the hammer components 74, however, are oriented in opposite directions on the two hammermills 71 and 72.

As shown in FIG. 6, the rotating shaft 76 of each hammermill is supported by a pair of bearing means 77 carried by the hammermill housing 73. This bearing means is illustrated more clearly in FIG. 7 and includes a bearing support 91 supporting an annular bearing 92 in spaced relationship relative to the hammermill housing 73 to define a bearing support cavity 93 therein. A plurality of mounting bolts 94 are provided to mount the bearing and bearing support to the housing 73.

In order to permit effective rotation of the shaft 76 relative to the hammermill housing 73, there must be a slight clearance 95 between the shaft and the housing; and during operation of the hammermill, disinfectant solution will enter into the cavity 93 through clearance 95. In order to remove this liquid from the bearing, a flinger element 96 in the form of an annular disk is positioned within the cavity and is mounted to and rotatable with the shaft 76. As the hammermill is operating, liquid entering into cavity 93 will be "flung" outwardly by centrifugal force from the flinger element and driven out of the bearing through bearing support drain 97.

Each of the hammer components 74 carried by each of the hammermills 71 and 72 is carried by, and is freely rotatable on, a plurality of pins 81. As many as 12 hammer elements can be carried on four pins securely fastened between a pair of supporting spider elements 82 that are fixed to the rotating shafts 76 of the hammermills. The rod-like elements may be steel rod that are one to three inches by ¼ to ½ inch in cross section and are three to twelve inches long that are carried on pins ½ to one inch in diameter. The clearance between the two hammermills at their closest point is approximately ½ inch.

During normal operation, the hammermills 71 and 72 rotate in opposite directions at high speeds, for example, at 3,500 rpm, (as indicated by arrows 84 and 86) of FIG. 5; and the hammer components 74 strike the solid waste materials, breaking them into smaller and smaller pieces within a container surrounding the hammermills. After the flailing hammer elements have continued to strike and break the solid waste for a period of time, the solid waste becomes sufficiently reduced in size to enable it to pass through the openings 83 in the lower part of the container into a transition chute 66 (FIG. 5) which directs the particles and disinfectant fluid to conduit 18 leading to the separator. The transition chute should have a smooth inside surface to prevent any hang-up of the debris flowing therethrough. By utilizing a disintegrator formed with two large counter-rotating hammermills, even large articles (as large as 16 inches square by 48 inches long) can be reliably disintegrated to a size generally small enough to pass through openings 83 each of which have a diameter of ½ inch. In the preferred embodiment, each hammermill is provided with eightyeight openings to minimize the risk of debris blockage.

Figure 8:
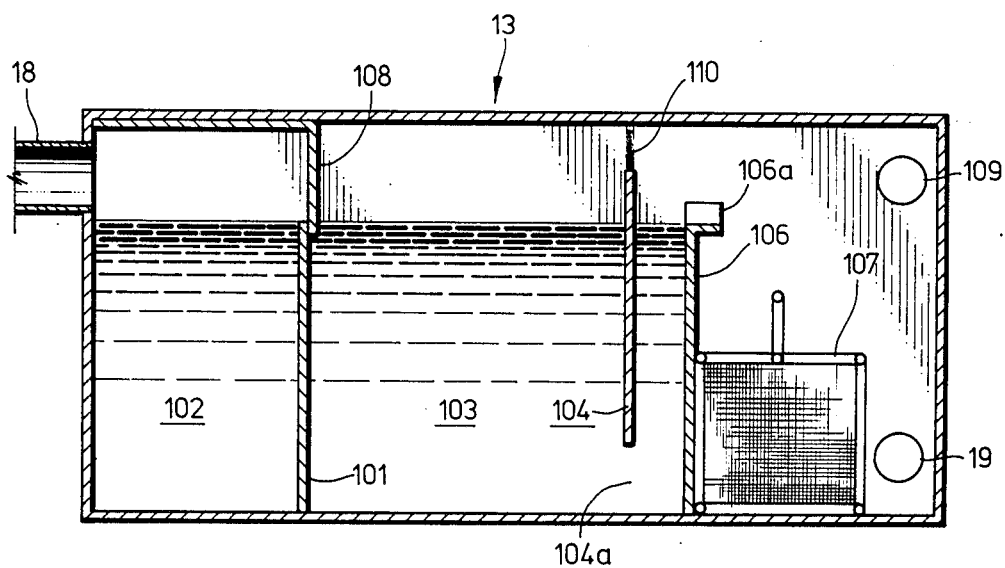
FIG. 8 is a cross-sectional view of the separator portion of the system.

With reference now to FIG. 8, disintegrated waste and disinfectant travel through conduit 18 from the cabinet 11 to separator 13. The separator includes a plurality of partitions to separate the solid waste and disinfectant solution. One partition 101 forms a first weir forming a first collecting pool 102 for the collection of solid waste, which is heavier than the solution, from the disinfectant solution by gravity. Disinfectant solution and those portions of solid waste light enough to escape the first collection pool 102 flow over the first weir 101 into a second collection pool 103 formed by a second weir-forming partition 104. Additional settling of hospital waste through gravity occurs in the second pool 103, while floating waste is trapped by the further partition 104 in the second pool. This partition is supported within the separator above the bottom to define an opening 104a adjacent the bottom of the second pool. As a result of this arrangement, disinfectant solution is drawn from the bottom of the second pool and flows over weir portion 106a, thus largely trapping any remaining solid waste in the second pool.

An air deflector 108 is positioned within the separator to deflect any blowing air from the hammermill into collecting pool 102 and to prevent any liquid carried by the air from flowing directly into the HEPA filter hose assembly 109. A "hogs hair" filter 110 is also provided, as shown, to catch any airborne liquid that might not be blocked by deflector 108.

For even greater assurance that solid waste will not be delivered into the public sewer system, flow over the weir portion 106a is directed into a foraminous container 107 as a final trap for solid waste. The disinfectant solution flows through the openings in the foraminous container and outwardly from the separator 13 into the public sewer through conduit 19. The solid waste which has been reduced to particulate form can periodically be removed from the separator and placed in large containers or bags for disposal.

The system controller 14 includes microprocessor systems and associated electronics for monitoring and controlling the overall operation of the waste disposal system 10. The system is provided with a "soft" start-up in order to prevent any sudden power surges and transients in the general hospital electrical system. For example, a "Nordic ES-3" control is used to control voltage and current during start-up. The controller includes means for monitoring the current level on the hammermill motors 54 to detect any overload that may occur within the hammermills and to take corrective action before any damage can result to the system.

On the detection of a disintegrator motor overload current, the microprocessor acts to stop the feeding means 12 after a first period of time (e.g., seven seconds), to prevent the feeding of additional waste materials to the hammermills. The hammermills continue to operate, however, to disintegrate and clear the waste already in the disintegrator. If after a second period of time (e.g., twelve seconds), the current is still too high, clearance trap doors in the hammermill container (doors 87 in FIG. 6) are opened by a pneumatic cylinder 80 to more rapidly clear the disintegrator of waste. If the current is still too high after a third period of time (e.g., seventeen seconds), the motors 54 will be stopped and caused to reverse for sixty seconds while the trap doors 87 remain open to insure complete clearing of the hammermills.

As indicated above, the exhaust of the negative pressure system is filtered to prevent the delivery of contaminated air to the hospital environment. The filter system includes a two-stage system including a HEPA filter. The system controller includes sensors to monitor the pressure drop across the filter system and to provide a warning, for example, by a warning light at the user control station, when the H.E.P.A. filter needs to be cleared or changed. The flow of disinfectant from the disinfectant source 45 is also monitored by flow switches 68 and 69 in disinfectant lines 62 and 63. When there is no disinfectant flow through the flow switches 68 and 69 for seven seconds, the control system stops the movement of conveyor belt 22. Refilling of the disinfectant source or removal of disinfectant flow blockage will permit the system to be restarted.

The system is also provided with an orderly, automatic shutdown sequence. Upon operation of the system stop switch, the hammermill motors are reversed for sixty seconds with trapdoors 87 opened. The second conveyor means is flushed with water for about three minutes; and the filter system blower 46 continues to operate for ninety minutes to clear the system of contaminated air. The logic then goes to a start-up program.

Other protective features can be incorporated into the system to provide a highly reliable, substantially automatic system.

Although a specific embodiment of the system is shown and described, other embodiments and arrangements may be devised using the subject matter of this invention without departing from the scope of the following claims.

I claim:

1. Apparatus for disposing of contaminated waste, comprising:
   a generally sealed cabinet;
   feeding means for feeding contaminated waste into said cabinet, said feeding means including first conveyor means capable of receiving a plurality of contaminated articles, and second conveyor means for automatically transferring said contaminated articles into said cabinet one at a time;

disintegrator means in said cabinet for disintegrating said waste articles fed into said cabinet, said disintegrator means comprising a pair of counter-rotating hammermill means;

decontaminating means including a decontaminating fluid in said cabinet for decontaminating said waste articles fed into said cabinet;

separator means for separating disintegrated and decontaminated waste articles from said decontaminating fluid; and a normally closed door blocking access into said cabinet from said feeding means, and wherein said second conveyor means includes means for opening said door when a contaminated article is to be transferred into said cabinet.

2. Apparatus for disposing of contaminated waste which includes:

disintegrator means for disintegrating said contaminated waste;

feeding means for feeding said contaminated waste to said disintegrator means, said feeding means including continuous conveyor means for receiving said contaminated waste to be fed to said disintegrator means;

said continuous conveyor means comprising a first conveyor portion for receiving said contaminated waste and wherein said feeding means, further comprises a second conveyor portion for receiving said contaminated waste from said first conveyor portion and for transferring said contaminated waste to said disintegrator means, said second conveyor portion including an inclined surface for receiving said contaminated waste from said first conveyor portion and means for moving said contaminated waste along said inclined surface into said disintegrator means, said moving means comprising a motor driven belt assembly positioned above said inclined surface, said belt assembly including belt means for engaging said waste and for moving said waste along said inclined surface into said disintegrator means, said belt assembly occupying an upwardly extended position proximate to said first conveyor portion and a downwardly extended position proximate to said disintegrator means;

decontaminating means including a decontaminating fluid for decontaminating said waste;

separator means for separating said disintegrated waste from said decontaminating fluid; and door means for blocking access to said disintegrator means, and means coupling said belt assembly to said door means for opening said door means when waste is to be transferred into said disintegrator means.

3. Apparatus as recited in claim 2 wherein said belt assembly includes means for mounting said belt assembly for pivotal movement around the end remote from said door means, and wherein an article of waste being moved by said belt means causes said belt assembly to pivot around said end remote from the door means and lift the opposite end of the belt assembly and open said door means by an amount necessary to allow said article of waste to pass into said disintegrator means.

4. Apparatus as recited in claim 3 wherein said door means includes an upper portion and a lower portion that are pivotally interconnected, the upper portion being pivotally carried by said second conveyor portion housing and the lower portion being pivotally attached to said opposite end of the belt assembly.

5. A waste disposal apparatus for treating and disposing of infectious contaminated waste on a substantially continuous basis in a substantially controlled closed aseptic environment, and for continuously converting said contaminated waste into a safely disposable noninfectious and nontoxic residue through the thorough disintegration and disinfection of such waste, said apparatus comprising:

continuous feeding conveyor means for continuously transferring and feeding said contaminated waste to a disintegrator delivery position;

first disintegrator means operably positioned to receive said contaminated waste from said disintegrator delivery position for disintegrating said waste into substantially small waste fragments for said further substantially continuous treatment and disposal of same by and from said apparatus;

second disintegrator means operably positioned adjacent said first disintegrator means for further disintegration of said contaminated waste;

said first and second disintegrator means collectively comprising a pair of counter-rotating motor-driven hammermill means for violently disintegrating said contamined waste at a substantially high speed;

disintegrator sealing means operably positioned after said continuous feeding conveyor means and before said first disintegrator means to preclude against the release of contamination from said contaminated waste disintegrating within said first and second disintegrator means;

decontaminating means operably positioned adjacent at least one of said first and second disintegrator means and including a decontaminating fluid for decontaminating said waste therewithin; and separator means for separating said disintegrated waste from said decontaminating fluid.

6. Apparatus as recited in claim 5 wherein said continuous feeding conveyor means further includes a conveyor housing, said continuous feeding conveyor means being supported within said conveyor housing; and wherein said apparatus further within said conveyor housing for preventing the escape includes means for maintaining a negative air pressure of contaminated air therefrom.

7. Apparatus as recited in claim 6 wherein said continuous conveyor feeding means comprises an endless belt.

8. Apparatus as recited in claim 6 and further including split curtain means comprising a spit-back curtain assembly operably positioned within said conveyor housing for blocking the escape of particles from the disintegrator means and for maintaining the negative pressure within the conveyor housing.

9. Apparatus as recited in claim 8 wherein said split curtain means comprises a plurality of spit-back curtain assemblies operably positioned at spaced locations along the length of said conveyor housing.

10. Apparatus as recited in claim 6 wherein said means for maintaining a negative air pressure within said conveyor housing comprises blower means within said housing.

11. Apparatus as recited in claim 5 and further including control means for controlling the rate at which said contaminated waste is continuously fed to said disintegrator means by said feeding means.

12. Apparatus as recited in claim 5 wherein said continuous conveyor feeding means comprises a first conveyor portion for receiving said contaminated waste and wherein said continuous conveyor feeding means further comprises a second conveyor portion for receiving said contaminated waste from said first conveyor portion and for transferring said contaminated waste to said first and second disintegrator means.

13. Apparatus as recited in claim 12 wherein said second conveyor portion includes an inclined surface for receiving said contaminated waste from said first conveyor portion and means for moving said contaminated waste along said inclined surface into said first and second disintegrator means.

14. Apparatus as recited in claim 13 wherein said moving means comprises a motor driven belt assembly positioned above said inclined surface, said belt assembly including belt means for engaging said waste and for moving said waste along said inclined surface into said first and second disintegrator means, said belt assembly occupying an upwardly extended position proximate to said first conveyor portion and a downwardly extended position proximate to said disintegrator means.

15. Apparatus as recited in claim 14 wherein said belt assembly pivots about the axis of a belt assembly roller operably positioned at said upwardly extended position, said belt assembly being urged by gravity downwardly towards said downwardly extended position, said belt means having a toothed surface for engaging said waste.

16. Apparatus as recited in claim 5 and further including means for monitoring said first and second disintegrator hammermill means for an overloaded condition, said monitoring means including means for monitoring the current level on the motors driving said hammermill means.

17. Apparatus as recited in claim 16 and further including means for effecting a soft start-up of one or more of said first and second disintegrator hammermill means to avoid power surges.

18. Apparatus as recited in claim 16 and further including means for initiating an overload clearing sequence upon the detection of an overload condition.

19. Apparatus recited in claim 5 in which said disintegrator sealing means comprises door means operably positioned between said continuous feeding conveyor means and one or more of said first and second disintegrator means for alternatively blocking and providing access to said first and second disintegrator means as desired, said door means opening to provide access to said disintegrator means as said contaminated waste is transferred thereto from said continuous feeding conveyor means.

20. Apparatus as recited in claim 5 wherein said decontaminating means includes means for feeding said decontaminating fluid to said hammermill means, and wherein said disintegrator means includes a hammermill housing, said pair of hammermill means being supported within said hammermill housing, each of said hammermill means including a rotating shaft extending through said hammermill housing and supporting a plurality of hammer elements within said hammermill housing, and bearing means for mounting said shaft to said housing.

21. Apparatus as recited in claim 20 wherein said hammermill housing and said rotating shaft extending therethrough defines a clearance therebetween through which decontaminating fluid can pass from said hammermill means into said bearing means, and wherein said bearing means includes means for defining a cavity for receiving said decontaminating fluid and means for removing said decontaminating fluid from said cavity.

22. Apparatus as recited in claim 21 wherein said removing means includes drain means in a wall of said bearing means in communication with said cavity, and flinger means positioned within said cavity and mounted to said shaft and rotatable therewith, the rotation of said flinger means driving decontaminating fluid within said cavity out of said cavity through said drain means by centrifugal force.

* * * * *

UNITED STATES PATENT AND TRADEMARK OFFICE
CERTIFICATE OF CORRECTION

PATENT NO. : 4,619,409
DATED : October 28, 1986
INVENTOR(S) : Harper et al.

It is certified that error appears in the above-identified patent and that said Letters Patent is hereby corrected as shown below:

Col. 10, Line 44      After "further" insert -- includes means for maintaining a negative air pressure --

Col. 10, Line 45      After "escape" delete "includes means for"

Col. 10, Line 46      Before "of" delete "maintaining a negative air pressure"

Signed and Sealed this

Twenty-first Day of April, 1987

Attest:

DONALD J. QUIGG

Attesting Officer      Commissioner of Patents and Trademarks